(12) United States Patent
Rupp et al.

(10) Patent No.: US 8,685,070 B2
(45) Date of Patent: Apr. 1, 2014

(54) FACETED BONE SCREW

(75) Inventors: Glenn A. Rupp, Cramerton, NC (US); Scott Duquette, Clemmons, NC (US)

(73) Assignee: Medical Facets, LLC, Port Washington, NY (US)

(*) Notice: Subject to any disclaimer, the term of this patent is extended or adjusted under 35 U.S.C. 154(b) by 0 days.

(21) Appl. No.: 13/372,161

(22) Filed: Feb. 13, 2012

(65) Prior Publication Data

US 2012/0150238 A1 Jun. 14, 2012

Related U.S. Application Data

(63) Continuation-in-part of application No. 11/985,960, filed on Nov. 19, 2007, now Pat. No. 8,112,870.

(51) Int. Cl.
*A61B 17/86* (2006.01)

(52) U.S. Cl.
USPC .......................................... 606/309

(58) Field of Classification Search
USPC ......... 411/411, 413, 308–311, 417, 420, 421; 433/172–174, 73, 201.1; 606/300–331
See application file for complete search history.

(56) References Cited

U.S. PATENT DOCUMENTS

| | | | |
|---|---|---|---|
| 2,393,131 A | 1/1946 | Vang | |
| 3,201,967 A | 8/1965 | Balamuth et al. | |
| 3,783,668 A | 1/1974 | Dawson et al. | |
| 3,879,974 A | 4/1975 | Biddell et al. | |
| 4,419,912 A | 12/1983 | Sotome et al. | |
| 4,782,688 A | 11/1988 | Kawashima | |
| 5,159,167 A | 10/1992 | Chaikin et al. | |
| 5,288,714 A | 2/1994 | Marschke | |
| 5,395,195 A | 3/1995 | Fulmer | |
| 5,702,443 A | 12/1997 | Branemark | |
| 5,725,573 A | 3/1998 | Dearnaley et al. | |
| 6,431,869 B1 * | 8/2002 | Reams et al. | 433/174 |
| 6,450,748 B1 | 9/2002 | Hsu | |
| 6,595,733 B1 | 7/2003 | Willert | |
| 7,217,195 B2 | 5/2007 | Matsubayashi | |
| 7,559,221 B2 | 7/2009 | Horita et al. | |
| 7,875,285 B1 | 1/2011 | Roorda et al. | |
| 7,879,086 B2 | 2/2011 | Davis | |
| 7,901,453 B2 | 3/2011 | Ragheb et al. | |
| 7,913,642 B2 | 3/2011 | O'Connor et al. | |
| 8,028,646 B2 | 10/2011 | Pui et al. | |
| 2002/0127084 A1 * | 9/2002 | Hsu | 411/387.4 |
| 2004/0121848 A1 | 6/2004 | Zhang | |
| 2005/0076751 A1 | 4/2005 | Panasik et al. | |

(Continued)

FOREIGN PATENT DOCUMENTS

EP 1 493 399 1/2005

*Primary Examiner* — Christopher Beccia
(74) *Attorney, Agent, or Firm* — Tutunjian & Bitetto, P.C.

(57) ABSTRACT

A faceted bone screw and a method for manufacturing the same includes a screw thread configuration having facets that are incorporated into one or more of the leading edge, trailing edge or root of the thread. The facets are generally made up of a plurality of transitioning peaks and valleys which vary the depth of the thread and are disposed in one or more locations throughout the threaded portion of the bone screw. The facets operate to reduce the torque required to drive the bone screw into bone, while at the same time operate to assist in anchoring the bone screw within the bone once inserted therein, and thereby reduce the possibility for the screw backing out after insertion.

6 Claims, 8 Drawing Sheets

(56) References Cited

U.S. PATENT DOCUMENTS

| | | |
|---|---|---|
| 2005/0208095 A1 | 9/2005 | Hunter et al. |
| 2006/0162142 A1 | 7/2006 | Manuel |
| 2006/0225477 A1 | 10/2006 | Takemasu et al. |
| 2008/0004693 A1 | 1/2008 | Burgess et al. |

\* cited by examiner

FACETED BONE SCREW

CROSS REFERENCE TO RELATED APPLICATIONS

This application is a Continuation-in-Part of U.S. patent application Ser. No. 11/985,960 filed on Nov. 19, 2007, now U.S. Pat. No. 8,112,870.

BACKGROUND

1. Technical Field

The present principles relate to orthopedic (bone) screws. More particularly, it relates to an orthopedic screw with facets implemented in one or more of the leading edge and trailing edges of the thread form.

2. Description of Related Art

Medical screws or Orthopedic (bone) screws or threaded pins are commonly used in orthopedic procedures where it is required to set a bone or multiple bones in a position that is secure with respect to either 1) the adjacent bone or bone part for which the screw is used; or 2) the surgical splint or other external fixation device that is maintained in position using the bone or orthopedic screw. As used herein, the term "bone screw" and/or "orthopedic screw" are interchangeably used herein and shall include all known medical and orthopedic screws and threaded pins that are used human and/or animal bones.

One common concern in the use of bone screws is the splitting of the bone during the insertion of the screw. Splitting often occurs when the workpiece (e.g., bone) is brittle by nature, and the friction between the screw and the bone requires higher torques to sufficiently penetrate the bone for proper application.

Another concern is the potential for the screws to loosen or "back out" after installation. This loosening can result in the mis-setting of a bone and require supplemental procedures to be performed to correct the same.

It is would therefore be desirable to have a bone screw that eliminates these problems without requiring any change in the current approved procedures for the installation and withdrawal of such bone screws.

SUMMARY

The faceted bone screw of the present principles will operate to reduce the friction between the screw and the bone, thereby reducing the torque required to drive the screw and/or threaded pins into the bone. This torque reduction can thereby assist in lowering the rate of splitting osteoporotic bone particularly around the shaft of the screw while the bone screw is inserted.

The faceted bone screw of the present principles will also reduce the likelihood of bone screws and threaded pins backing out of the bone due to improved osteointegration between the faceted threaded portion of the implanted device and the bone.

According to one implementation, the orthopedic screw includes a shaft, a thread cut into at least a portion of said shaft, the threads having a leading edge, a trailing edge and a depth, and at least one facet formed in one of the leading edge or the trailing edge of the thread, where the at least one facet increases a surface area of the respective leading or trailing edge.

Other aspects and features of the present principles will become apparent from the following detailed description considered in conjunction with the accompanying drawings.

It is to be understood, however, that the drawings are designed solely for purposes of illustration and not as a definition of the limits of the present principles, for which reference should be made to the appended claims. It should be further understood that the drawings are not necessarily drawn to scale and that, unless otherwise indicated, they are merely intended to conceptually illustrate the structures and procedures described herein.

BRIEF DESCRIPTION OF THE DRAWINGS

In the drawings wherein like reference numerals denote similar components throughout the views.

DETAILED DESCRIPTION

Figure 1:
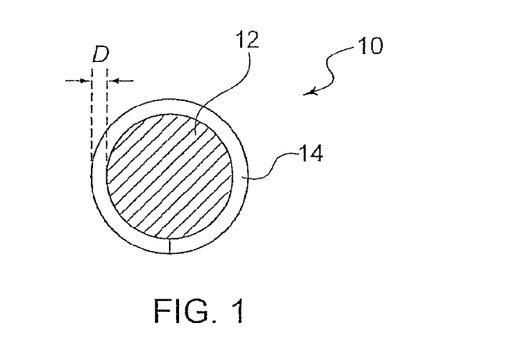
FIG. 1 is cross sectional view of a bone screw according to the prior art.

FIG. 1 shows a cross section of a bone screw 10 according to the prior art. The shaft 12 includes a thread 14 that can extend any length of the shaft 12, including the entire length of the same. The thread generally has a consistent non-variable depth D depending on the particular application for that screw. The pitch, which relates to the distance between adjacent threads, is also generally consistent for most bone screws and fasteners.

Those of ordinary skill in the art will recognize that one or more different portions of the shaft 12 can include threads 14, or alternatively the entire shaft 12 can be threaded. These same concepts apply to the bone screw of the present principles.

Figure 2A:
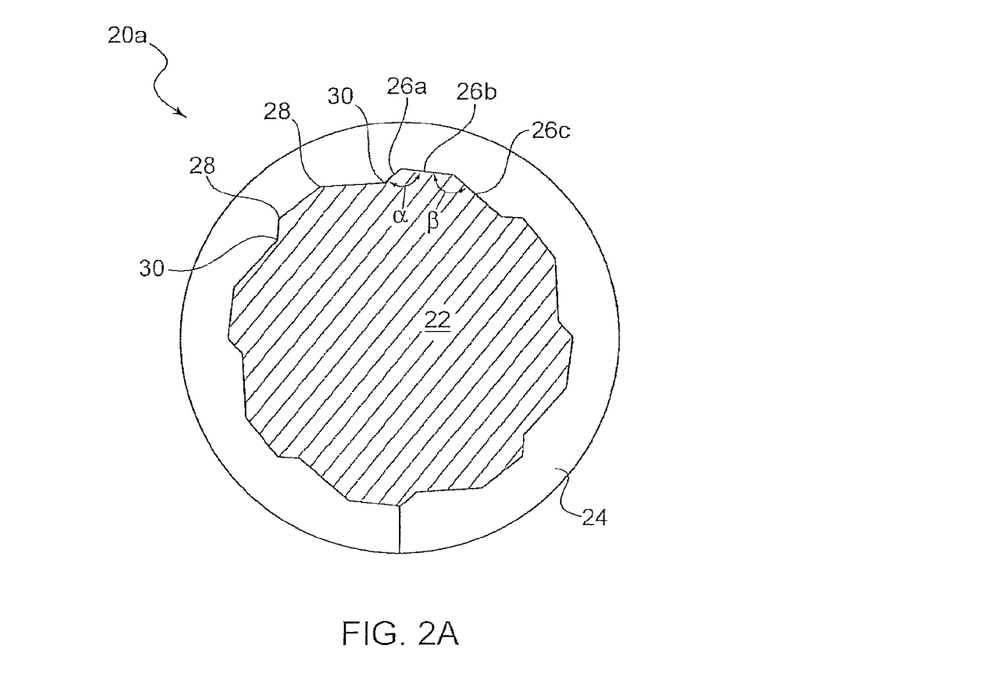
FIGS. 2a and 2b are cross-sectional views of a faceted bone screw according to an implementation of the present principles.

FIG. 2a shows a cross section of a faceted bone screw 20 according to an implementation of the present principles. The bone screw 20 has a shaft 22 having threads 24 which include one or more facets 26a, 26b and 26c. These facets are generally transverse to the thread groove and extend across the same for some or part of the overall thread length. Although shown transverse to the thread, it is contemplated that the facets may be offset from a pure transverse relationship with the thread groove. By incorporating facets 26 into the shaft within the thread groove 24, a plurality of peaks 28 and valleys 30 are formed therein. The facets 26 are disposed at different angles α and β with respect to the next adjacent facet. The angles a can be in a range of 90-170 degrees while the angles B can be in a range of 100-175 degrees. The implementation of the facets 26 will provide for a varying depth D of the thread.

As shown, there are several peaks 28 and valleys 30 formed by the facets 26 at varying depths within the thread, each having rising/falling sides depending on the direction of rotation of the shaft 22. These peaks and valleys, in conjunction with the rising/falling sides operate to reduce the friction between the bone and the screw and thereby operate to reduce the torque required to drive the bone screw into and remove from a bone. As will be appreciated, when the shaft 22 is rotated in one direction, the rising sides of the respective peaks will gradually operate to penetrate the bone and once the peak is met, the friction between the bone and the screw thread is substantially reduced as the bone passes over the falling side of that peak.

By repeating this process in a series like configuration throughout the thread, the overall torque required to drive the bone screw can be reduced by up to 50% (depending on the size of the screw and the bone being penetrated).

Once inserted into the bone, the bone will permit osteointegration with the facets 26 (including the peaks and valleys), and the facets become like anchors for preventing the screw from loosening (i.e., "backing out") after inserted by the doctor. However, when the bone screw must be extracted, a simple application of torque in the loosening direction will cause the bone to loosen or break free from the facets 26, and facets will once again operate to reduce the torque in required in the removal of the bone screw.

Figure 2B:
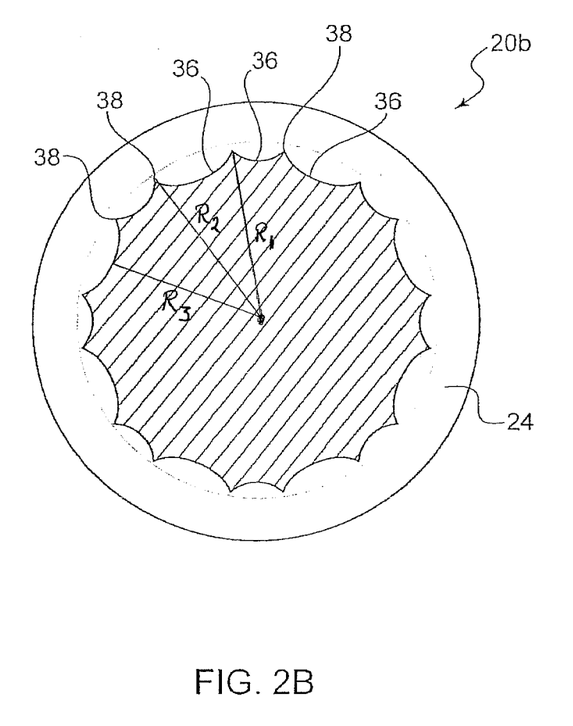

FIG. 2b shows another implementation of the bone screw 20 where the facets 36 are concave in nature and the peaks are designated by the points 38 between the respective concave facets 36. In this implementation, the valleys would be considered at the base of each concave facet 36, and the friction reduction would be omni-directional (i.e., work the same in both clockwise and counterclockwise directions). As shown, there are differing radii R1, R2, R3, etc. that results from the formation of the concave facets 36 and the corresponding peaks and valleys.

In order to manufacture the bone screw in a reproducible, certifiable manner, a precise manufacturing technique is employed using a Swiss type screw machine tool. Those of ordinary skill in the art will recognize that this time tuning (i.e., lathe) or multiple axis Swiss type CNC (Computer Numerically Controlled) screw machine is only one example of the type of machine that could be properly configured to manufacture the faceted bone screw disclosed herein, and that other types of machines may also be implemented without departing from the spirit of the present principles.

Figure 3A:
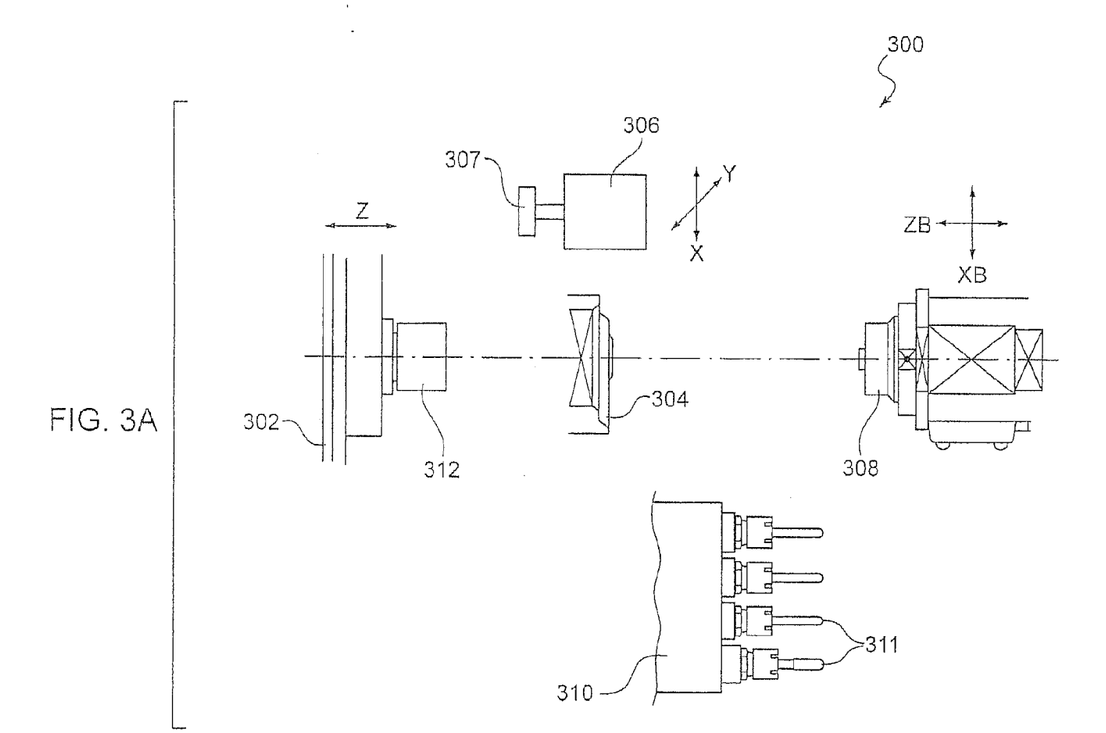
FIG. 3a is a plan view of the bone screw cutting machine that is used to manufacture the bone screw according to an implementation of the present principles.

FIG. 3a shows a plan view of a Swiss cutting machine 300 used to manufacture the bone screw of the present principles. This is the sliding headstock type CNC automatic lathe that is generally composed of a headstock 302, a guide bushing (or guide collet) 304, a live tool holder 306, a sub spindle 308, and a tool holder slide 310. The tool holder slide includes one or more tools or dies 311 that can be used during other cutting processes. Although shown here for exemplary purposes, the present principles may not require the tool holder slide 310 during the process of manufacturing the faceted bone screw.

The headstock 302 includes a main spindle 312 and a sliding unit (not shown). The main spindle 312 chucks a bar with the guide bushing 304 and provides it with rotary motion. The sliding unit provides reciprocating action on the material in the Z-axis direction (longitudinal) with the CNC control. Feeding of a bar in the Z axis direction is provided by the headstock during the main machining. The live tool holder 306 includes a tool or cutter 307 that cuts the thread onto the (wires) bar stock used to form the same.

Figure 3B:
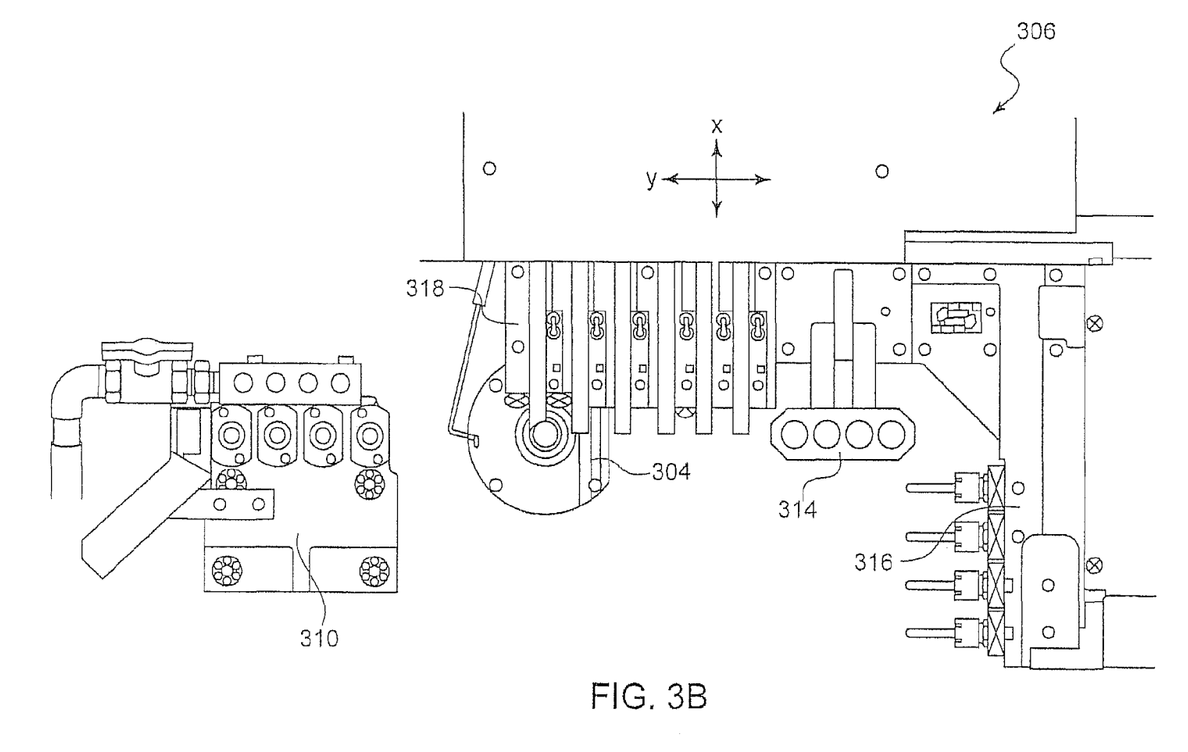
FIG. 3b is a plan view of the bone screw cutting machine that is used to manufacture the bone screw according to an implementation of the present principles.

FIG. 3b shows a plan view of the live tool holder 306 of the Screw cutting lathe/machine 300. The live tool holder is capable of reciprocating motion in the X-axis and Y-axis under the CNC Control, and will feed material in a diametric direction during main machining. The tool post makes the cutting tool contact the bar near the guide bushing 304 and cooperates with the headstock 302 to execute the machining. The tool holder (not shown), the 4-spindle sleeve holder 314 and the 4-spindle cross drilling/milling unit 316 are attached to the tool post. The cutting tool will be attached to the tool holder to execute turning.

The front machining tool holder is attached to the sleeve holder 314, and executes a front drilling, tapping and boring action. Power driven tools can be attached to the 4-spindle cross unit 316, providing a rotating motion for drilling, tapping and end milling, etc., to perform cross or front drilling, tapping and milling.

The X-axis performs a diameter direction feed of the tool holder and the tool selection of the 4-spindle cross drilling/milling unit. The Y-axis performs the tool selection of the tool holder, tool selection of the sleeve holder 314 and a diameter direction feed of the 4-spindle cross drilling/milling unit 316.

Figure 3C:
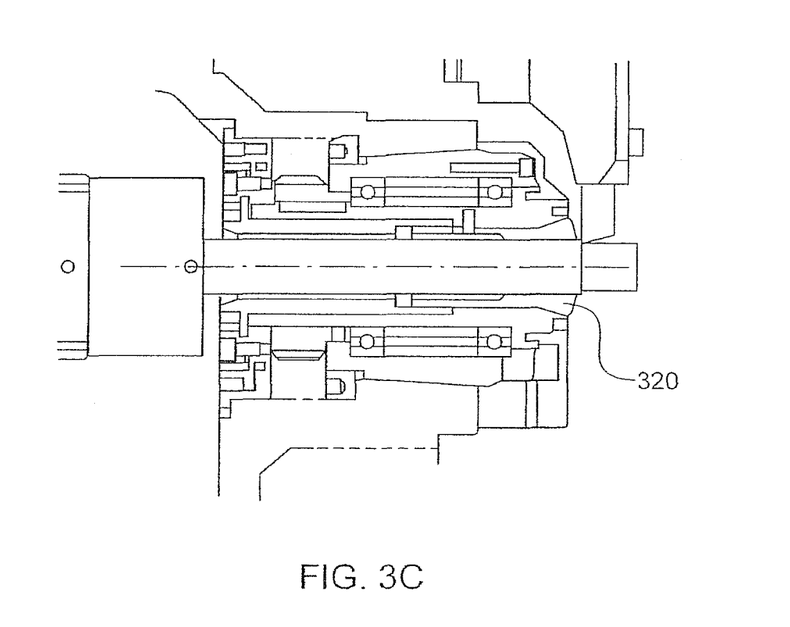
FIG. 3c is a plan view of the revolving guide bush of the screw cutting machine used to manufacture the bone screw of the present principles.

The guide bushing 304 supports a bar near the machining position to prevent material from bending, and thereby helps to achieve highly accurate and reproducible machining. In this unit, the guide bushing 304 supports most of the cutting load in the diametric direction, and the machining accuracy is somewhat dependent on the clearance between the guide bushing 304 and the bar. Therefore, selection of the bar is based on the precision required for the outer diameter of the material being cut with the threads of the present principles. The guide bushing 304 is preferably a revolving guide bush 320 (see FIG. 3c) that is synchronized with the main spindle. Generally the guide bush 320 is positioned within the guide bushing 304.

The sub spindle 313 chucks a bar with the guide bushing (collet) 304 and provides a rotary motion. The sliding unit provides material reciprocation in the ZB-axis direction (longitudinal) and the XB-axis direction with the CNC control.

The tool holder 310 provides ZB-axis direction feed in the back machining, and XB-axis direction feed in the tool selection of sub-spindle unit 308. The various roles of the back attachment machining can be roughly classified as follows:

Non-pip machining: The back attachment chucks a work piece in the cutting process and performs the cutting process by synchronous rotation with the main spindle so as to obtain a cutting-off surface without dowel.

Z-ZB synchronous control: The back attachment chucks a work piece at the same time with the main spindle during the main machining. It also performs a synchronous operation in direction of the Z/ZB-axis, or makes a synchronous rotation with a main spindle so that it suppresses bending or warping of the bar.

Back machining: The live tool holder 306 performs back machining of the cutting-end surface and periphery thereof in cooperation with the back sub-spindle unit 308 of the tool post.

Sub-spindle unit 308 <This is not included in type 540S of the machine>: The tool holder 306 for machining of the cutting-end surface is attached to the back machining sub-spindle unit 308 to perform the backside drilling, tapping and boring. Selecting the drive system for power driven attachment (this is an option) permits the attachment of a power-driven tool until and the machining of the back off-center tapping/milling.

Figure 4:
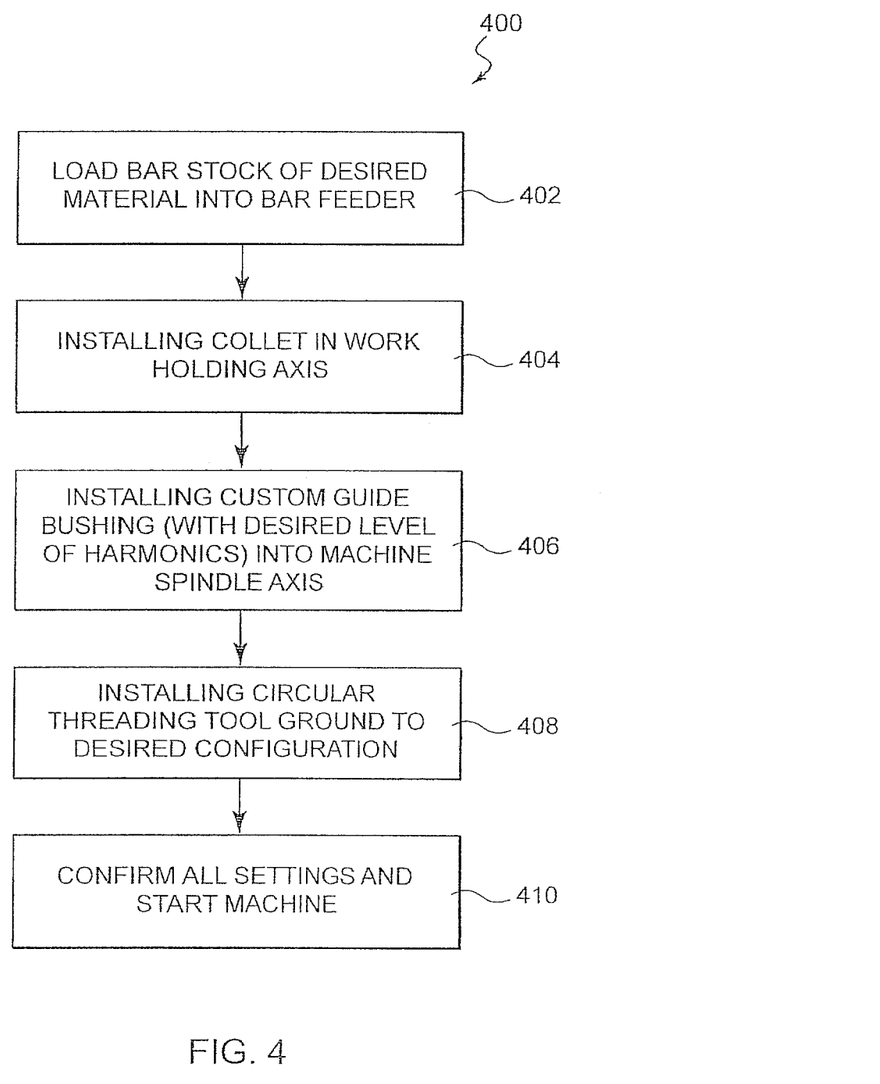
FIG. 4 is a flow diagram of the method for manufacturing a faceted bone screw according to an implementation of the present principles.

FIG. 4 shows the method 400 for manufacturing the faceted bone screw in accordance with a semi-automatic implementation. In accordance with one method of the present principles, a bar stock of desired material is loaded (402) into the bar feeder. A collet is installed (404) in the work holding axis. A custom made guide bushing, fabricated to the size require to produce a desired level of clearance related harmonics, is installed (406) into the machine spindle axis. A circular threading tool which has been ground to produce the desired thread configuration is installed (408) one a live tool holder.

According to one aspect, the facets of the faceted bone screw are applied through a precisely controlled vibratory effect through the application of clearance related harmonics during the screw cutting process. Thus, by adjusting the size of the guide bushing (guide collet) we can define the clearing between the same and the bar stock. This "clearance" generates a clearance related harmonic (or a controlled vibratory effect) as the bar stock is fed through the spindle axis passing by the rotating circular threading tool which is generating the thread configuration onto the bar stock. Through the control of the clearance, the vibratory effect is accurately controlled. Examples of such clearance would be 0.0002-0.005 inches.

Those of skill in the art will recognize that the Swiss type screw machine is a computer programmable machine, and as such, the aforementioned processed can be computer controlled by the machine once programmed accordingly. For example, the machine can be programmed so the threading tool produces the thread configuration in one pass or multiple passes, depending on the size of the bar stock, the amount of material to be machined, and desired finish.

Other multiple features of the faceted bone screw can be performed prior to, or after, the thread configuration is generated onto the bar stock, such as screw head generation, drilling pilot details, drive configurations, coatings and/or any further surface preparation treatments, etc.

Figure 5:
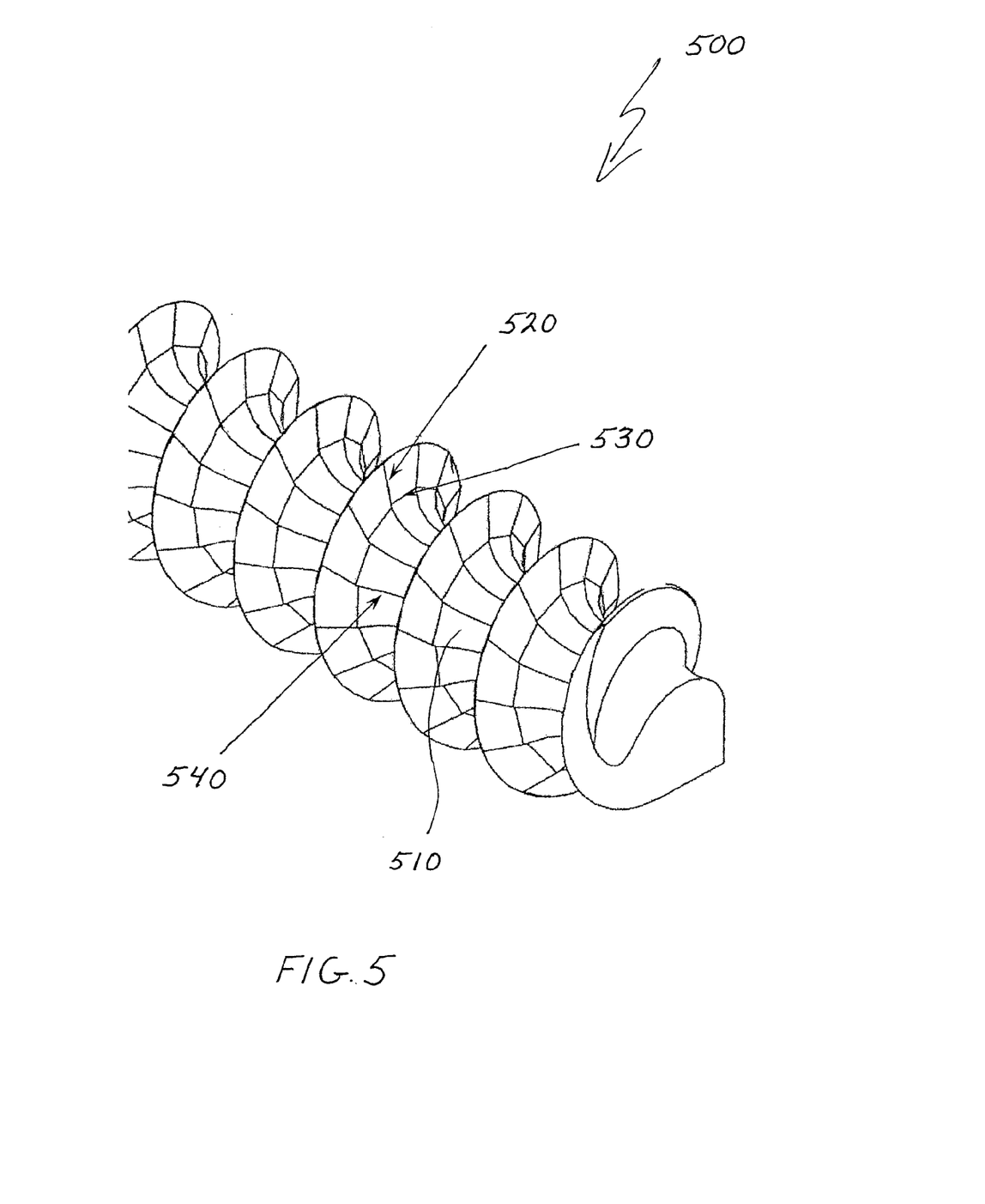
FIG. 5 shows another alternative multi-facet thread configuration for a bone/orthopedic screw according to another implementation of the present principles.

FIG. 5 shows yet another implementation of the faceted bone screw 500 according to the present principles. As is shown, the facets 510 are generally trapezoidal in shape. The facets 510 can have peak parallel to the thread groove and can also have multiple peaks, some transvers to the thread groove while adjacent peaks are parallel to the thread groove. As shown, the facet peak 520 is generally transverse to the thread groove on the leading face of the thread. The facet peak 530 is generally parallel to the thread groove, and the facet peak 540 is generally transverse to the thread groove on the root of the thread.

Figure 6A:
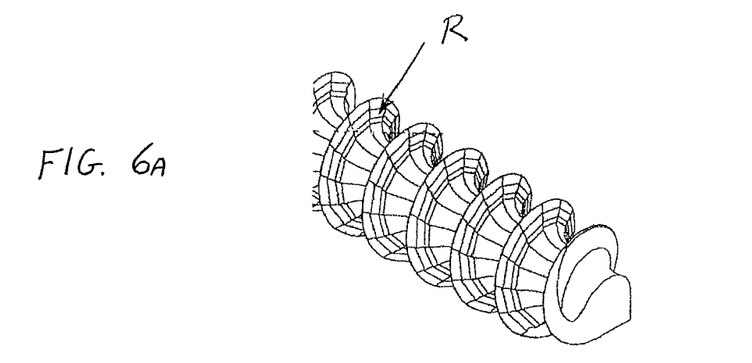
FIGS. 6a-6c show further alternative multi-facet thread configurations for a bone/orthopedic screw according to yet another implementation of the present principles.
Figure 6B:
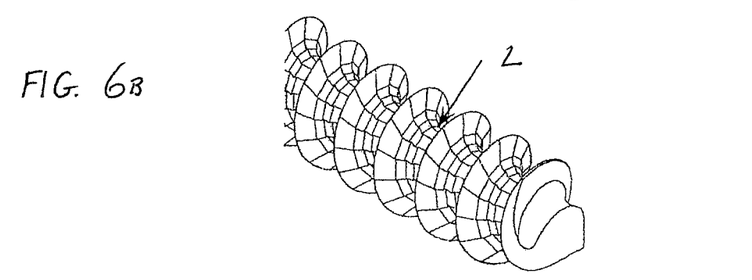
Figure 6C:
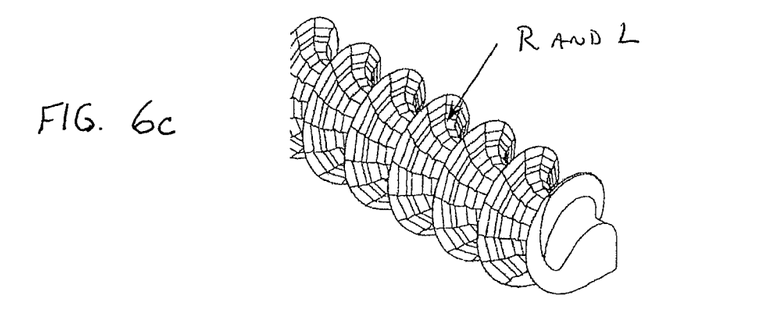

FIGS. 6a-6c show examples of the multiple facets disposed in various directions. FIG. 6A shows multiple facets in the radial (R) direction. FIG. 6B shows multiple facets in the longitudinal direction (L). FIG. 6C shows multiple facets in the radial (R) and longitudinal (L) direction.

In accordance with other implementations, the bone screw of the present principles may be manufactured and then coated with medications or other treatments that promote osteointegration, prevent infection and/or deliver one or more medications in one or more varying volumes to the areas around the bone screw (i.e., either the areas of bone around the screw that is inserted into the bone and/or the areas of bone screw that are not within the bone but are still within the patient's body). Some examples of such coatings and method for applying them can be found in U.S. Pat. Nos. 7,875,285, 7,879,086, 8,028,646, 7,913,642 and 7,901,453, each of which is incorporated herein by reference. Those of skill in the art will appreciate that any coating or treatment could be added to the bone/orthopedic screw of the present principles without departing from the scope of the same. This may include films or coatings that dissolve once within the human body. Other possible coatings or files may also include those that facilitate bone growth (e.g., bone growth hormones).

Those of skill in the art will recognize that the "bar stock" referred to throughout this specification is the material which the orthopedic/bone screw is made of Examples of this material, as they are currently being used are Titanium, Stainless Steel, cobalt chromium, and absorbable biocompatible plastics. The present principles may apply to any known or not yet known material used for orthopedic/bone applications.

It is to be understood that the present principles may be implemented in various forms of hardware, software, firmware, special purpose processors, or a combination thereof. Preferably, the present principles may be implemented as a combination of hardware and software. Moreover, the software is preferably implemented as an application program tangibly embodied on a program storage device. The application program may be uploaded to, and executed by, a machine comprising any suitable architecture. Preferably, the machine is implemented on a computer platform having hardware such as one or more central processing units (CPU), a random access memory (RAM), and input/output interface(s). The computer platform also includes an operating system and microinstruction code. The various processes and functions described herein may either be part of the microinstruction code or part of the application program (or a combination thereof) that is executed via the operating system. In addition, various other peripheral devices may be connected to the computer platform such as an additional data storage device and a printing device.

It is to be further understood that, because some of the constituent system components and method steps depicted in the accompanying Figures are preferably implemented in software, the actual connections between the system components (or the process steps) may differ depending upon the manner in which the present principles is programmed. Given the teachings herein, one of ordinary skill in the related art will be able to contemplate these and similar implementations or configurations of the present principles.

While there have been shown, described and pointed out fundamental novel features of the present principles, it will be understood that various omissions, substitutions and changes in the form and details of the methods described and devices illustrated, and in their operation, may be made by those skilled in the art without departing from the spirit of the same. For example, it is expressly intended that all combinations of those elements and/or method steps which perform substantially the same function in substantially the same way to achieve the same results are within the scope of the present principles. Moreover, it should be recognized that structures and/or elements and/or method steps shown and/or described in connection with any disclosed form or implementation of the present principles may be incorporated in any other disclosed, described or suggested form or implementation as a general matter of design choice. It is the intention, therefore, to be limited only as indicated by the scope of the claims appended hereto.

What is claimed is:

1. An orthopedic screw comprising:
   a shaft;
   a thread cut into at least a portion of said shaft, said threads having a leading edge, a trailing edge, and a depth, wherein said leading and trailing edges are not part of the shaft; and
   at least one facet formed in one of the leading edge or the trailing edge of the thread.

2. The orthopedic screw of claim 1, wherein said at least one facet comprises a plurality of facets.

3. The orthopedic screw of claim 2, wherein the plurality of facets are radially cut into the leading or trailing edge of the thread.

4. The orthopedic screw of claim 2, wherein the plurality of facets are longitudinally cut into the leading or trailing edge of the thread.

5. The orthopedic screw of claim 2, wherein the each of the plurality of facets are cut into the leading or trailing edge of the thread with a varying radii with respect to the shaft.

6. The orthopedic screw of claim 2, further comprising at least one facet disposed on shaft of the screw between adjacent threads.

* * * * *